United States Patent [19]

Chasar

[11] 4,415,686

[45] Nov. 15, 1983

[54] STERICALLY HINDERED PHENYL BIS(NAPHTHYL)PHOSPHITES AND COMPOSITIONS THEREOF

[75] Inventor: Dwight W. Chasar, Northfield, Ohio

[73] Assignee: The B. F. Goodrich Company, Akron, Ohio

[21] Appl. No.: 444,280

[22] Filed: Nov. 24, 1982

[51] Int. Cl.$^3$ .................... C07F 9/145; C08K 5/52
[52] U.S. Cl. ............................ 524/101; 252/404; 252/400 A; 260/941; 260/967; 524/151
[58] Field of Search ............... 252/400.24; 260/941, 260/967; 524/101, 151

[56] References Cited

U.S. PATENT DOCUMENTS

| | | | |
|---|---|---|---|
| 2,058,343 | 10/1936 | Moran et al. | 260/967 |
| 2,220,845 | 11/1940 | Moyle | 260/967 |
| 3,415,907 | 12/1968 | Sconce et al. | 260/967 |
| 3,637,582 | 1/1972 | Gilles | 524/101 |
| 3,909,491 | 9/1975 | Gilles | 524/101 |
| 4,025,486 | 5/1977 | Gilles | 524/101 |
| 4,066,608 | 1/1978 | Van Brederode | 524/101 |
| 4,094,855 | 6/1978 | Spivack | 524/151 |
| 4,185,004 | 1/1980 | Mathis | 524/101 |
| 4,360,617 | 11/1982 | Muller et al. | 524/101 |

*Primary Examiner*—John Kight, III
*Assistant Examiner*—R. A. White
*Attorney, Agent, or Firm*—J. Hughes Powell, Jr.; Nestor W. Shust

[57] ABSTRACT

2,6-Di-t-butyl-4-substituted phenyl bis(3,6-di-t-butyl-2-naphthyl)phosphites, readily prepared by reacting together a phosphorodichloridite of a 4-substituted-2,6-di-t-butylphenol and a sodium salt of 3,6-di-t-butyl-2-naphthol, to form antioxidant and ultraviolet stabilizers that form particularly effective combinations with hydroxyphenylalkyleneyl isocyanurates to provide enhanced oven aging properties to organic materials subject to attack by heat and oxygen.

20 Claims, No Drawings

STERICALLY HINDERED PHENYL BIS(NAPHTHYL)PHOSPHITES AND COMPOSITIONS THEREOF

BACKGROUND OF THE INVENTION

There has been extensive research directed to the preparation and evaluation of aryl phosphites as polymer stabilizers. While some of these have been made available commercially many of them have limited application because of deficiencies that limit their general application. Typical of these deficiencies are lack of hydrolytic stability, both on the shelf and in use, and in a particular application, undesirable potential water carry over in polypropylene processing. Improved aryl phosphites that provide heat and oxygen resistant antioxidant compositions when combined with hydroxyphenylalkyleneyl isocyanurates are desired that also are resistant to hydrolysis.

SUMMARY OF THE INVENTION 2,6-di-t-butyl-4-substituted phenyl bis(3,6-di-t-butyl-2-naphthyl)phosphites are effective antioxidants and provide protection against ultraviolet radiation in organic materials subject to degradation by heat, oxygen and ultraviolet radiation. These phosphites enhance antioxidant protection when combined with hydroxyphenylalkyleneyl isocyanurates in organic materials subject to attack by heat and oxygen, particularly in polymers, including polyolefins.

DETAILED DESCRIPTION

The 2,6-di-t-butyl-4-substituted phenyl bis(3,6-di-t-butyl-2-naphthyl)phosphites of this invention have the following general formula:

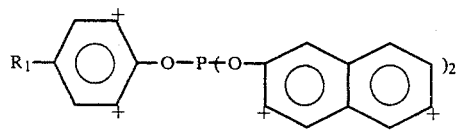

wherein

+ is t-butyl or t-pentyl;

$R_1$ is hydrogen, an alkyl radical containing 1 to 9 carbon atoms, a cycloalkyl radical containing 3 to 6 carbon atoms, halogen, an alkoxy radical containing 1 to 8 carbon atoms, phenyl, a t-alkyl radical containing 4 to 8 carbon atoms, and a

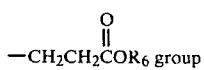

where $R_6$ is an alkyl radical containing 1 to 8 carbon atoms.

In a preferred group of compounds:

+ is t-butyl, $R_1$ is hydrogen, a primary, secondary or tertiary alkyl radical containing 1 to 4 carbon atoms and the

wherein $R_6$ is methyl or ethyl.

The sterically hindered phenyl bis(naphthyl)phosphites are readily prepared from totally hindered phenols such as 4-substituted-2,6-di-t-butylphenols and the lesser hindered phenol 3,6-di-t-butylnaphthol. The procedure to form the defined 4-substituted-2,6-t-butylphenyl bis(3,6-di-t-butyl-2-naphthyl)phosphite is to react a phosphorodichloridite of the 4-substituted-2,6-di-t-butylphenols with a sodium salt of 3,6-di-t-butyl-2-naphthol.

The completely hindered phenols for preparing the phenyl bis(naphthyl)phosphites have the general formula

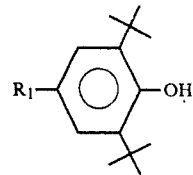

wherein:

+ is t-butyl or t-pentyl; and $R_1$ is hydrogen, an alkyl radical containing 1 to 9 carbon atoms, a cycloalkyl radical containing 3 to 6 carbon atoms, halogen, an alkoxy radical containing 1 to 8 carbon atoms, phenyl, a t-alkyl radical containing 4 to 8 carbon atoms, and a

where $R_6$ is an alkyl radical containing 1 to 8 carbon atoms.

A preferred group of phenols are those wherein + is t-butyl, $R_1$ is hydrogen, a primary, secondary or tertiary alkyl group of 1 to 4 carbon atoms and the

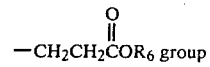

where $R_6$ is methyl or ethyl.

Typical totally hindered phenols are 2,6-di-t-butyl-4-methylphenol, 2,6-di-t-butyl-4-ethylphenol, 2,6-di-t-butyl-4-isopropylphenol, 2,4,6-tri-t-butylphenol, 2,6-di-t-butyl-4-n-butylphenol, 2,6-di-t-butyl-4-(2-carbethoxyethyl)phenol, 2,6-di-t-pentyl-4-methylphenol, and the like.

Typical phenyl bis(naphthyl) phosphites of this invention were prepared as described in the following Examples. In each preparation, the named structure was confirmed by nuclear magnetic resonance and infrared spectra.

EXAMPLE I 2,6-di-t-butyl-4-methylphenyl bis(3,6-di-t-butyl-2-naphthyl)phosphite was prepared as follows. 3,5-di-t-butyl-2-naphthol was converted to the sodium salt, sodium 3,6-di-t-butyl-2-naphthylate, by reacting it with sodium hydride. 0.75 gram (0.031 mol) of sodium hydride as a 50% dispersion in mineral oil was added to 8.0 grams (0.031 mol) of 3,6-di-t-butyl-2-naphthol dissolved in 75 ml of dry tetrahydrofuran. The mixture was heated at 50° C. for one hour to form the sodium salt. The phosphorodichloridite was prepared by reacting 78.9 grams (0.36 mol) of 2,6-di-t-butyl-4-methylphenol with 150 grams (1.1 mol) of phosphorus trichloride in the presence of 42 grams of a triethylene amine catalyst at about 80° C. for 6 hours to form the 2,6-di-t-butyl-4-methylphenylphosphorodichloridite that was isolated by filtration and distillation. 5.0 grams (0.015 mol) of the 2,6-t-butyl-4-methylphenylphosphorodichloridite in 25 ml of dry tetrahydrofuran was added at room temperature under a nitrogen atmosphere to a solution of 8.7 grams (0.03 mol) of sodium 3,6-di-t-butyl-2-naphthylate dissolved in 75 ml of dry tetrahydrofuran. The reaction mixture was stirred at room temperature for 2 hours, filtered, and the filtrate evaporated to dryness. The recovered reaction product was a glass and it was washed with an acetonitrile to give a white solid. The melting point was 247°–250° C. The molecular weight determined by field desorption/mass spectrometry was 760.

EXAMPLE II 2,4,6-tri-t-butylphenyl bis(3,6-di-t-butyl-2-naphthyl)-phosphite was prepared as described herein. 3,6-di-t-butyl-2-naphthol was converted to the sodium salt, sodium 3,6-di-t-butyl-2-naphthylate, by reacting it with sodium hydride. 0.8 gram (0.03 mol) of sodium hydride as a 50% dispersion in mineral oil was added to 8.5 grams (0.033 mol) of 2,6-di-butyl-2-naphthol dissolved in 100 ml of dry tetrahydrofuran. The mixture was heated at 50° C. for one hour to form the sodium salt. The phosphorodichloridite was prepared by reacting 28.4 grams (0.11 mol) of 2,4,6-tri-t-butylphenol with 50 grams (0.36 mol) of phosphorus trichloride in the presence of 13.2 grams of a triethyl amine catalyst at about 80° C. for 6 hours to form the 2,6-di-t-butyl-4-methylphenylphosphorodichloridite that was isolated by filtration and distillation. 6.05 grams (0.16 mol) of the 2,4,6-tri-t-butylphenylphosphorodichloridite in 25 ml of dry tetrahydrofuran was added at room temperature under a nitrogen atmosphere to a solution of 9.23 grams (0.033 mol) of sodium 3,6-di-t-butyl-2-naphthylate dissolved in 75 ml of dry tetrahydrofuran. The reaction mixture was stirred at room temperature for 2 hours, filtered, and the filtrate evaporated to dryness. The recovered reaction product was a solid and it was washed with acetonitrile to give a white powder. The molecular weight determined by FD/MS was 802.

EXAMPLE III 2,6-di-t-butyl-4-n-butyl bis(3,6-di-t-butyl-2-naphthyl)-phosphite was prepared by the following procedure. 3,6-di-t-butyl-2-naphthol was converted to the sodium salt, sodium 3,6-di-t-butyl-2-naphthylate, by reacting it with sodium hydride. 0.86 gram (0.0358 mol) of sodium hydride as a 50% dispersion in mineral oil was added to 9.2 grams (0.0358 mol) of 3,6-di-t-butyl-2-naphthol dissolved in 100 ml of dry tetrahydrofuran. The mixture was heated at 50° C. for one hour to form the sodium salt. The phosphorodichloridite was prepared by reacting 56.8 grams (0.22 mol) of 2,6-di-t-butyl-4-n-butylphenol with 100 grams (0.73 mol) of phosphorus trichloride in the presence of 26.4 grams of a triethyl amine catalyst at about 80° C. for 7 hours to form the 2,6-di-t-butyl-4-n-butylphenylphosphorodichloridite that was isolated by filtration and distillation. 6.5 grams (0.0179 mol) of the 2,6-t-butyl-4-methylphenylphosphorodichloridite in 25 ml of dry tetrahydrofuran was added at room temperature under a nitrogen atmosphere to a solution of 10 grams (0.036 mol) of the sodium 3,6-di-t-butyl-2-naphthylate dissolved in 75 ml of dry tetrahydrofuran. The reaction mixture was stirred at room temperature for 2 hours, filtered, and the filtrate evaporated to dryness. The recovered reaction product was a tan glass and it was washed with acetonitrile to give a white powder, melting point 211°–216° C. The molecular weight determined by field desorption/mass spectrometry was 802.

Following this procedure, the following compound was prepared from the named reactants.

2,6-di-t-butyl-4-(2-carbethoxyethyl) bis(3,6-di-t-butyl-2-naphthyl)phosphite, from 3,6-di-t-butyl-2-naphthol and 2,6-di-t-butyl-4-(2-carbethoxyethyl)phenol.

Test samples of the triaryl phosphites in polypropylene were prepared by mixing the stabilizer compounds with polypropylene in a Brabender Plasticoder fitted with a Cam-Head (mixing chamber). The polypropylene is first masticated for $1\frac{1}{2}$ minutes at 190° C. Then the stabilizer is added, followed by 3 minutes additional mixing. The mass is removed and pressed into 20 mil thick sheets. From these sheets are cut $1'' \times 1''$ plaques for oven aging. Type C ($3'' \times \frac{1}{8}''$) tensil bars are cut for UV stability tests.

Thermal/oxidative stability (oven aging) testing consisted of aging the samples in triplicate in an air-circulating oven at 125° C. The time of catastrophic crumbling (failure) of the plaque was measured and reported as days to failure.

Each sample contained 0.1 weight part of triaryl-phosphite per 100 weight parts of polypropylene. The following results were obtained:

2,6-di-t-butyl-4-methylphenyl bis(3,6-di-t-butyl-2-naphthyl)phosphite—$8\frac{5}{8}$ days.

2,4,6-tri-t-butylphenyl bis(3,6-di-t-butyl-2-naphthyl)-phosphite—9 days.

2,6-di-t-butyl-4-n-butyl bis(3,6-di-t-butyl-2-naphthyl)-phosphite—$8\frac{5}{8}$ days.

Samples containing 0.1 weight part of triarylphosphite were tested for ultraviolet light stability, i.e., resistance to degradation by UV radiation. The samples were tested in an Atlas Xenon Weatherometer, Model No. 65-WR, equipped with a 6500 watt Xenon burner tube in accordance with ASTM #D2565-79-A. The black panel temperature was 60° C. The samples were subjected to an 18 minute water cycle every two hours. The time in hours to a 50% loss in tensile strength was determined. For comparison purposes tris-β-naphthyl phosphite) was tested and found to have lost 50% tensile strength after 160 hours. The following results were obtained:

2,6-di-t-butyl-4-methylphenyl bis(3,6-di-t-butyl-2-naphthyl)phosphite—1300 hours.

2,4,6-tri-t-butylphenyl bis(3,6-di-t-butyl-2-naphthyl)-phosphite—650 hours.

2,6-di-t-butyl-4-n-butyl bis(3,6-di-t-butyl-2-naphthyl)-phosphite—640 hours.

2,6-di-t-butyl-4-(2-carbethoxyethyl) bis(3,6-di-t-butyl-2-naphthyl)phosphite—660 hours.

The hydroxyphenylalkyleneyl isocyanurate compounds used in combination with the triaryl phosphites of this invention have the formula

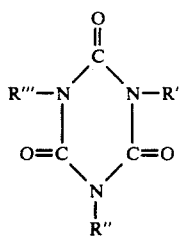

wherein R' is a hydroxyphenylalkyleneyl radical of the formula

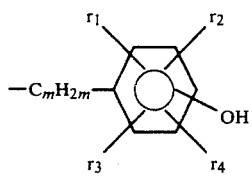

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R''' are hydrogen, an alkyl radical containing 1 to 18 carbon atoms, or are the same as R'. A more preferred compound is when R" and R''' are equal to R', i.e., all the R groups are hydroxyphenylalkyleneyl radicals, and $r_1$ is a t-alkyl radical containing from 4 to about 12 carbon atoms, $r_2$ is an alkyl radical containing from 1 to about 12 carbon atoms, $r_3$ and $r_4$ are hydrogen, and m=1.

Even more preferred are the symmetrical tris (3,5-di-tert-alkyl-4-hydroxybenzyl) isocyanurates of the formula

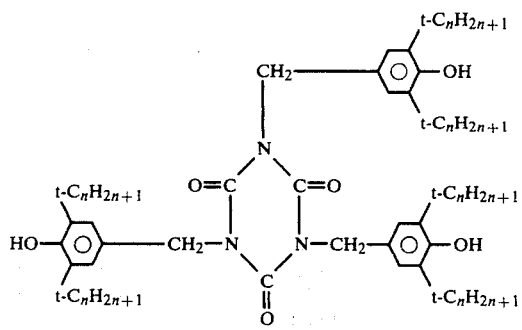

where n is 4 to 8.

Examples of the 4-hydroxybenzyl isocyanurate compounds are: tris-3-t-butyl-4-hydroxybenzyl) isocyanurate, tris-(3-cetyl-4-hydroxybenzyl) isocyanurate, tris(3,5-dimethyl-4-hydroxybenzyl) isocyanurate, tris-(3-methyl-5-isopropyl-4-hydroxybenzyl) isocyanurate, tris (3,5-di-t-butyl-4-hydroxybenzyl) isocyanurate, tris-(3-t-butyl-5-t-amyl-4-hydroxybenzyl) isocyanurate, tris-[3,5-di-(1-methyl-1-ethylpropyl)4-hydroxybenzyl] isocyanurate, tris-[3,5,-di-(1,1,2,2-tetramethylpropyl)-4-hydroxybenzyl] isocyanurate, bis-(3,5-dimethyl-4-hydroxybenzyl) isocyanurate, (3-methyl-4-hydroxybenzyl) isocyanurate, (3-t-butyl-4-hydroxybenzyl) isocyanurate, and the like. Reference is made to U.S. Pat. No. 3,531,483 which discloses isocyanurate compounds encompassed by this invention. The disclosure of this patent is incorporated herein by reference.

The amount of triaryl phosphite used may vary from about 0.01 to 10 weight parts per 100 weight parts of material to be stabilized. More usually about 0.1 to 4.0 parts are used for mixtures with the hydroxyphenylalkyleneyl isocyanurate. The hydroxyphenylalkyleneyl isocyanurate compound is used at a level from about 0.01 part to about 5 parts by weight, and more preferably at from about 0.05 part to about 3 parts by weight per 100 parts by weight of the organic material. The triaryl phosphite compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.1 to 6 parts by weight per 100 parts by weight of organic material. The hydroxyphenylalkyleneyl isocyanurate can be used in from about 10:1 to 1:10 weight ratio of isocyanurate compound to triaryl phosphite compound. Excellent results are obtained at about a 3:1 to 1:3 weight ratio. A 1:1 weight ratio of the compounds provides effective stabilization of organic materials.

To demonstrate the unexpected synergistic enhancement of antioxidant activity when the triaryl phosphites of this invention are combined with a hydroxyphenylalkyleneyl isocyanurate, test samples of polypropylene with 0.05 weight part each of tris (3,5-di-t-butyl-4-hydroxybenzyl) isocyanurate and the triaryl phosphites listed below were prepared and tested in the air oven until failure. The results obtained were as follows:

2,6-di-t-butyl-4-methylphenyl bis(3,6-di-t-butyl-2-naphthyl)phosphite—$100\frac{1}{3}$ days.

2,4,6-tri-t-butylphenyl bis(3,6-di-t-butyl-2-naphthyl)phosphite—100 days.

2,6-di-t-butyl-4-n-butyl bis(3,6-di-t-butyl-2-naphthyl)phosphite—$78\frac{2}{3}$ days.

A sample of polypropylene containing 0.1 weight part of tris(3,5-di-t-butyl-4-hydroxy-benzyl)isocyanurate failed after about $43\frac{1}{3}$ days. This is to be contrasted to the synergistic combination above wherein only 0.05 of the tris(3,5-di-t-butyl-4-hydroxy-benzyl)isocyanurate with 0.05 of the phenyl bis(naphthyl)phosphite did not fail for periods of 78 to 100 days.

These values also are better than those obtained with many commercially available phosphite stabilizers in the same compositions. For example, when these oven aging tests are repeated with 0.1 weight part of tris(2,4-di-t-butylphenyl)phosphite only, a value of 4 days was obtained. When repeated with this phosphite and the tris(3,5-di-t-butyl-4-hydroxy-benzyl)isocyanurate, in amounts of 0.05 weight parts each, a value of only $42\frac{1}{3}$ days was obtained.

The combinations of isocyanurate compound and the phenyl bis(naphthyl)phosphite compound as defined herein provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, polyisobutylene, and poly(4-methyl-1-pentene) have excellent resistance to ultra violet light when stabilized with the combinations of the present invention. Ethylene-propylene (EP) copolymers and ethylene-propylene (EPDM) terpolymers generally containing less than about 10 percent by weight of one or more monomers containing multiple unsaturation provided, for example, by 1,4-hexadiene, dimethyl-1,4,9-decatriene, dicyclopentadiene, vinyl norbornene, ethylidene norbornene and the like also are stabilized using the combination.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid, alkyl acrylates or methacrylates, methyl vinyl ketone, vinyl pyridine, etc.; polyisoprene, polychloroprene, and the like; vinyl polymers such as polyvinyl chloride, polyvinylidene chloride, copolymers of vinyl chloride with vinylidene chloride, polyvinyl acetate, copolymers or vinyl halide with butadiene, styrene, vinyl esters $\alpha,\beta$-unsaturated ketones and aldehydes, and the like; homopolymers and copolymers of acrylic monomers such as methyl acrylate, methyl methacrylate, ethyl acrylate, 3-ethylhexyl acrylate, acrylamide, methacrylamide, N-methylol-acrylamide, acrylonitrile, methacrylonitrile, and the like; epihalohydrin polymers; polyether- or polyol-derived polyurethanes; acetal homo-polymers and copolymers; polycarbonates; polyesters such as those derived from maleic, fumaric, itaconic, or terephthalic anhydrides, or the like; for example, polyethylene terephthalate; polyamides such as those derived from the reaction of hexa-methylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline, and the like.

The compounds are readily incorporated into materials by dissolving or dispersing them with the materials or in liquid, dispersion solutions and solid forms. If the material is a solid, especially a polymeric solid such as a rubber or a plastic, the compounds can be admixed using internal mixers as Banburys, extruders, two-roll mills, and the like, following conventional techniques. One way to disperse the compounds in plastic materials is to dissolve or suspend the compounds in a solvent, mix the mixture with a plastic in powder or solution form, and then evaporate the solvent.

Compositions containing the novel combination of compounds can also contain other known compounding ingredients such as fillers like carbon black, silica, metal carbonates, talc, asbestos, and the like; pigments and colorants; curative ingredients like sulfur and peroxides and vulcanization accelerators; fungicides; processing aids, reinforcing agents and standard ingredients known to the art. Other ingredients known in the art as ultra-violet light, thermal and/or oxidative stabilizers can also be used in the stabilized compositions.

I claim:

1. A hindered phenyl bis(naphthyl)phosphite having the formula

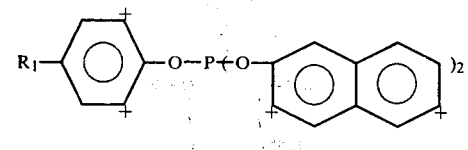

wherein

+ is t-butyl or t-pentyl; $R_1$ is hydrogen, an alkyl radical containing 1 to 9 carbon atoms, a cycloalkyl radical containing 3 to 6 carbon atoms, halogen, an alkoxy radical containing 1 to 8 carbon atoms, phenyl, a t-alkyl radical containing 4 to 8 carbon atoms, and a

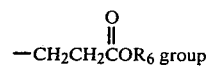

where $R_6$ is an alkyl radical containing 1 to 8 carbon atoms.

2. A phosphite of claim 1 wherein + is t-butyl, $R_1$ is hydrogen, a primary, secondary or tertiary alkyl radical containing 1 to 4 carbon atoms and the

wherein $R_6$ is methyl or ethyl.

3. A phosphite of claim 2, 2,6-di-t-butyl-4-methylphenyl bis(3,6-di-t-butyl-2-naphthyl)phosphite.

4. A phosphite of claim 2, 2,4,6-tri-t-butylphenyl bis(3,6-di-t-butyl-2-naphthyl)phosphite.

5. A phosphite of claim 2, 2,6-di-t-butyl-4-n-butyl bis(3,6-di-t-butyl-2-naphthyl)phosphite.

6. A composition comprising organic materials subject to degradation and stabilizing amounts of hindered phenyl bis(naphthyl)phosphites having the formula

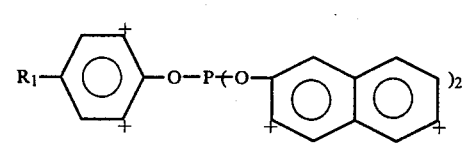

wherein

+ is t-butyl or t-pentyl; $R_1$ is hydrogen, an alkyl radical containing 1 to 9 carbon atoms, a cycloalkyl radical containing 3 to 6 carbon atoms, halogen, an alkoxy radical containing 1 to 8 carbon atoms, phenyl, a t-alkyl radical containing 4 to 8 carbon atoms, and a

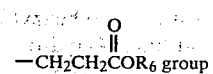

where $R_6$ is an alkyl radical containing 1 to 8 carbon atoms.

7. A composition of claim 6 wherein + is t-butyl, $R_1$ is hydrogen, a primary, secondary or tertiary alkyl radical containing 1 to 4 carbon atoms and the $$-CH_2CH_2COR_6$$

radical wherein $R_6$ is methyl or ethyl.

8. A composition of claim 7 wherein said organic material is a polymer and the phosphite is selected from the group consisting of 2,6-di-t-butyl-4-methylphenyl bis(3,6-di-t-butyl-2-naphthyl)phosphite, 2,4,6-tri-t-butylphenyl bis(3,6-di-t-butyl-2-naphthyl)phosphite and 2,6-di-t-butyl-4-n-butyl bis(3,6-di-t-butyl-2-naphthyl)-phosphite.

9. A stabilizer composition for organic materials comprising (1) hindered phenyl bis(naphthyl)phosphites having the formula

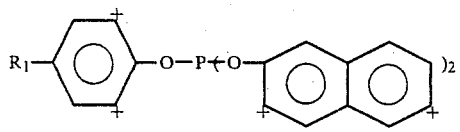

wherein
+ is t-butyl or t-pentyl; R₁ is hydrogen, an alkyl radical containing 1 to 9 carbon atoms, a cycloalkyl radical containing 3 to 6 carbon atoms, halogen, an alkoxy radical containing 1 to 8 carbon atoms, phenyl, a t-alkyl radical containing 4 to 8 carbon atoms, and a

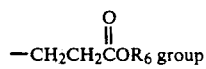

where R₆ is an alkyl radical containing 1 to 8 carbon atoms; and (2) hydroxyphenylalkyleneyl isocyanurates of the formula

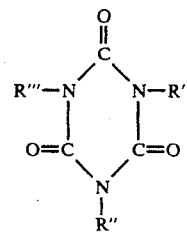

wherein R' is a hydroxyphenylalkyleneyl radical of the formula

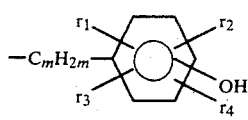

where m is 1 to 4, r₁ is an alkyl radical having 1 to 18 carbon atoms and is positioned immediately adjacent to the hydroxy group on the ring; r₂, r₃, and r₄ are hydrogen or an alkyl radical containing 1 to 18 carbon atoms; and R" and R'" are hydrogen, an alkyl radical containing 1 to 18 carbon atoms, or are the same as R'.

10. A stabilizer composition of claim 9 wherein in (1) + is t-butyl, R₁ is hydrogen, a primary, secondary or tertiary alkyl radical containing 1 to 4 carbon atoms and the

radical wherein R₆ is methyl or ethyl, and in (2) R" and R'" are equal to R', i.e., all the R groups are hydroxyphenyl-alkyleneyl radicals, and r₁ is a t-alkyl radical containing from 4 to about 12 carbon atoms, r₂ is an alkyl radical containing from 1 to about 12 carbon atoms, r₃ and r₄ are hydrogen, and m is 1.

11. A stabilizer composition of claim 10 wherein (2) has the formula

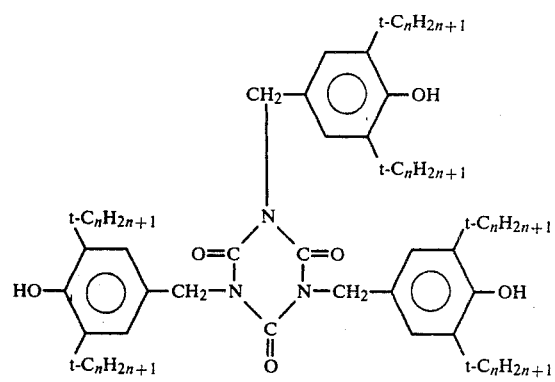

where n is 4 to 8.

12. A stabilizer composition of claim 11 where (2) is 1,3,5-tris(3,5-di-t-butyl-4-hydroxybenzyl)isocyanurate.

13. A stabilizer composition of claim 12 wherein (1) is selected from the group consisting of 2,6-di-t-butyl-4-methyl phenyl bis(3,6-di-t-butyl-2-naphthyl)phosphite, 2,4,6-tri-t-butylphenyl bis(3,6-di-t-butyl-2-naphthyl)-phosphite, and 2,6-di-t-butyl-4-n-butyl bis(3,6-di-t-butyl-2-naphthyl)phosphite.

14. A composition comprising organic materials subject to degradation and stabilizing amounts of (1) hindered phenyl bis(naphthyl)phosphites having the formula

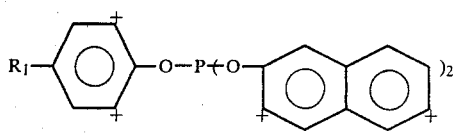

wherein
+ is t-butyl or t-pentyl; R₁ is hydrogen, an alkyl radical containing 1 to 9 carbon atoms, a cycloalkyl radical containing 3 to 6 carbon atoms, halogen, an alkoxy radical containing 1 to 8 carbon atoms, phenyl, a t-alkyl radical containing 4 to 8 carbon atoms, and a

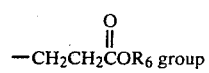

where R₆ is an alkyl radical containing 1 to 8 carbon atoms; and (2) hydroxyphenylalkyleneyl isocyanurates of the formula

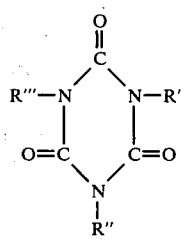

wherein R' is a hydroxyphenylalkyleneyl radical of the formula

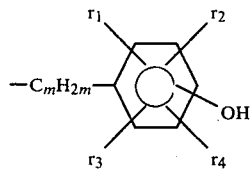

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R''' are hydrogen, an alkyl radical containing 1 to 18 carbon atoms, or are the same as R'.

15. A composition of claim 14 wherein said organic material is a polymer, in (1) + is t-butyl, $R_1$ is hydrogen, a primary, secondary or tertiary alkyl radical containing 1 to 4 carbon atoms and the

wherein $R_6$ is methyl or ethyl and in (2) R' and R''' are equal to R", $r_1$ is a tertiary alkyl radical containing 4 to 12 carbon atoms, $r_2$ is an alkyl radical containing 1 to 12 carbon atoms, $r_3$ and $r_4$ are hydrogen, and m is 1.

16. A composition of claim 15 wherein (2) has the formula

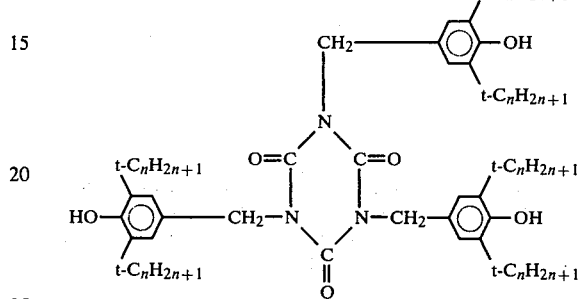

where n is 4 to 8.

17. A composition of claim 16 where (2) is 1,3,5-tris (3,5-di-t-butyl-4-hydroxybenzyl)isocyanurate.

18. A composition of claim 17, wherein said polymer is a polyolefin and (1) is 2,6-di-t-butyl-4-methylphenyl bis(3,6-di-t-butyl-2-naphthyl)phosphite.

19. A composition of claim 17, wherein said polymer is a polyolefin and (1) is 2,4,6-tri-t-butylphenyl bis(3,6-di-t-butyl-2-naphthyl)phosphite.

20. A composition of claim 17, wherein said polymer is a polyolefin and (1) is 2,6-di-t-butyl-4-n-butyl bis(3,6-di-t-butyl-2-naphthyl)phosphite.

* * * * *

UNITED STATES PATENT AND TRADEMARK OFFICE
CERTIFICATE OF CORRECTION

PATENT NO. : 4,415,686
DATED : November 15, 1983
INVENTOR(S) : Dwight William Chasar It is certified that error appears in the above-identified patent and that said Letters Patent are hereby corrected as shown below:

Claim 15, line 6 and 7 read "...(2) R' and R''' are equal to R'',...." This should read "(2) R'' and R''' are equal to R'..."

Signed and Sealed this

Eighteenth Day of December 1984

[SEAL]

Attest:

Attesting Officer

GERALD J. MOSSINGHOFF

Commissioner of Patents and Trademarks